United States Patent [19]

Eidem

[11] Patent Number: 4,832,294

[45] Date of Patent: May 23, 1989

[54] PORTABLE I.V. STAND

[75] Inventor: John C. Eidem, Burnsville, Minn.

[73] Assignee: Demstar Corporation, Burnsville, Minn.

[21] Appl. No.: 188,653

[22] Filed: Apr. 29, 1988

Related U.S. Application Data

[63] Continuation of Ser. No. 875,293, Jun. 17, 1986, abandoned.

[51] Int. Cl.⁴ ............................................. F16M 11/20
[52] U.S. Cl. .................................. 248/125; 248/145.6;
   248/312; 248/229; 248/129
[58] Field of Search ..................... 248/125, 129, 145.6,
   248/128, 229 R, 122, 124, 312, 121, 127, 188.7;
   D24/31; 604/245, 246

[56] References Cited

U.S. PATENT DOCUMENTS

| | | | |
|---|---|---|---|
| D. 269,121 | 5/1983 | Pollard | D24/31 |
| 460,250 | 9/1891 | Junkins | 248/129 X |
| 1,152,818 | 9/1915 | Kells | 604/246 X |
| 1,211,304 | 1/1917 | Farr | 604/80 X |
| 1,683,723 | 9/1928 | Myres | 604/80 X |
| 2,180,042 | 11/1939 | Ettinger | 248/132 X |
| 2,453,967 | 11/1948 | Browne | 248/122 |
| 2,964,202 | 12/1960 | Gingher et al. | 248/121 |
| 3,286,964 | 11/1966 | McMahan et al. | 248/188.7 |
| 3,479,973 | 11/1969 | Bartlett et al. | 248/188.7 |
| 4,030,690 | 6/1977 | Hanauer et al. | 248/125 X |
| 4,534,576 | 8/1985 | Jones, Jr. | 248/129 X |

FOREIGN PATENT DOCUMENTS

| | | | |
|---|---|---|---|
| 230759 | 4/1963 | Fed. Rep. of Germany | 248/121 |
| 171962 | 4/1966 | U.S.S.R. | 604/246 |

OTHER PUBLICATIONS

"Gee Clip" Publication, Henry A. Gardner Laboratory, Inc., Bethesda, MD.
Exhibit A—An advertisement for Porta-Pole TM Portable I.V. Equipment Pole Manufactured by Gray Wave—Appears on p. 26 of 2/87, Nutritional Services Mag.
Exhibit B—One Page Brochure Entitled "Pack It Up & Go! The New Click Lock IV Pole", Illustrating an IV Pole Sold by ICU Medical Inc.
Exhibit C—One Page Sales Letter from ICU Medical Inc. titled "Pack It Up + Go".

Primary Examiner—Robert W. Gibson, Jr.
Assistant Examiner—Karen J. Chotkowski
Attorney, Agent, or Firm—Merchant, Gould, Smith, Edell, Welter & Schmidt

[57] ABSTRACT

A portable stand (10) is provided for the transport of infusion pumps, intravenous solutions and other associated equipment. The stand consists of a T-shaped base (16) having a base member (18) with a base leg (20) extending perpendicularly therefrom. Large, diameter non-swiveling wheels (28) are located at either end of the base member (18) and the caster wheel (22) is located at the end of the base leg (20). A skid member (46) is provided to assist in the transport of the stand on stairs. A cylinder support platform (23) may be affixed to the T-shaped base (16).

20 Claims, 4 Drawing Sheets

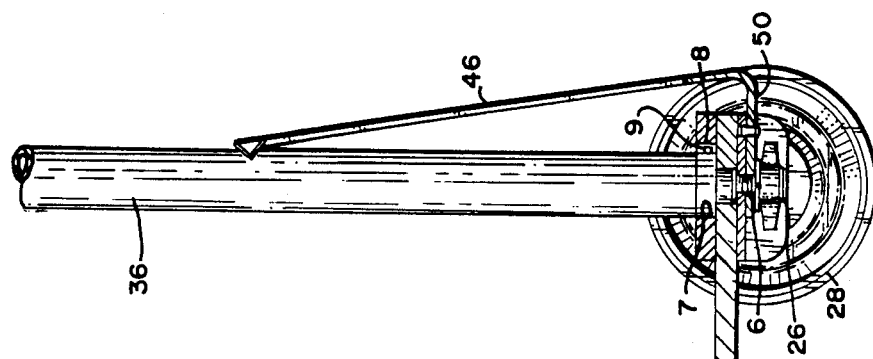
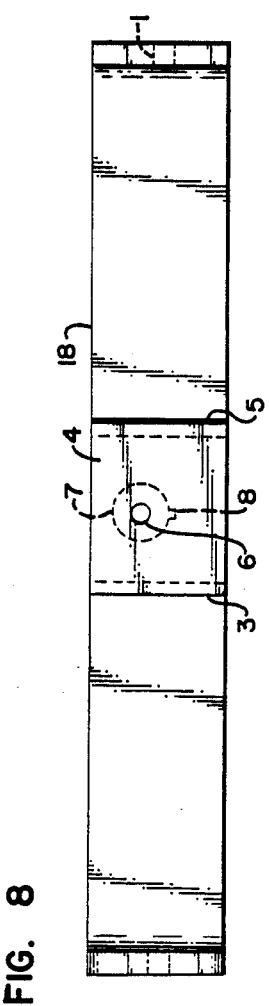
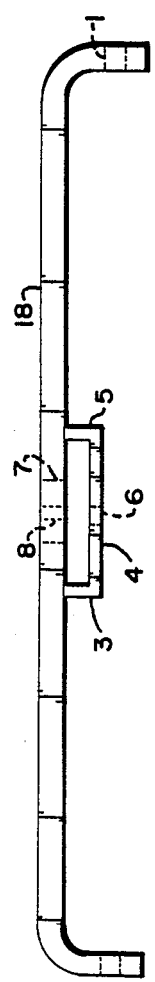
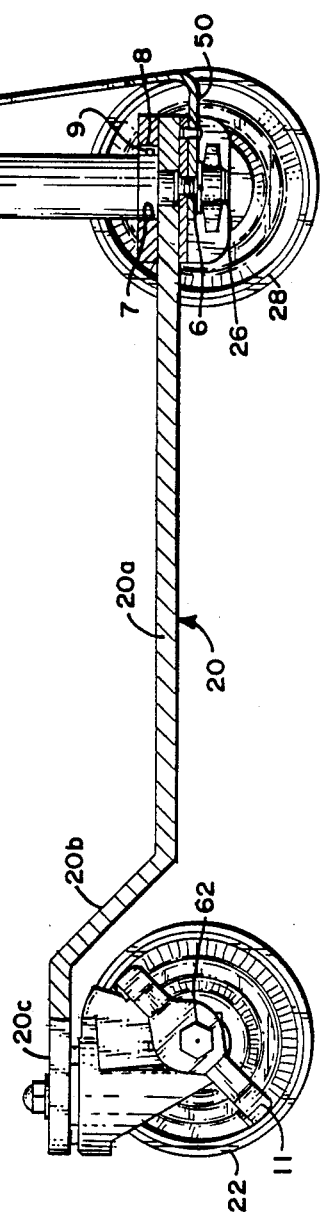
FIG. 8
FIG. 9
FIG. 2

PORTABLE I.V. STAND

This is a continuation, of application Ser. No. 875,293, filed June 17, 1986 abandoned.

FIELD OF THE INVENTION

The present invention relates generally to mobile equipment stands or racks. Specifically, the present invention is a portable, mobile stand suitable for supporting bottles or other fluid containers, and includes provisions for supporting cylindrical, gas containing vessels.

BACKGROUND OF THE INVENTION

For many years, intravenous (I.V.) solutions have been administered in a fairly simple fashion with a bottle or bag of solution hanging from a pole on a simple tripod base stand. Such solutions were traditionally administered in hospitals and there was little, if any, need for transport of such stands and other associated equipment. Recently, several advances in medicine have rendered such equipment obsolete. In particular, the development of infusion pumps has allowed the very precise control of the rate and amounts of administration of I.V. solution to the patient. While such pumps are portable in the broadest sense, they remain heavier than the traditional equipment associated with I.V. administration. In particular, in recent years home parenteral nutrition (HPN) has allowed effective treatment of patients with inadequate digestive systems due to accidents or disease. In particular, HPN is the administration of all required nutrients through a catheter into the bloodstream thereby bypassing the patient's regular digestive system. HPN, then, has allowed the treatment of a number of patients to be accomplished at home without requiring the institutionalization of such patients as was formerly the case.

The spread of the use of I.V. equipment to the home has rendered existing I.V. stands inadequate for several reasons. In the home, the patient is often reasonably ambulatory and thus, it will be highly desirable to transport the infusion pump and/or associated equipment with the patient about the house. Homes typically have various irregular surfaces which are not easily accommodated by conventional I.V. stands. In particular, such surfaces are stairs, carpets and any other surfaces which are not typical in an institutional setting.

Mobile equipment stands have numerous applications not related to the supply of intravenous fluids. For example, other medical conditions require the supply of various substances, such as oxygen, to the patient on a more or less continuous basis. Such substances may be typically stored in pressurized containers, usually of a cylindrical design. Due to the unique shape of the containers, and the fact that oxygen users are not likely to also require supplies of intravenous fluid, stands designed to facilitate oxygen transport have necessarily been dedicated to that exclusive use. Thus, the supply of oxygen and the supply of I.V. fluids constitute two separate needs which have not heretofore been merged into a single, covertible mobile equipment stand.

Previous stands have not proven effective due to their generally small wheels as well as their extreme susceptibility to tipping, especially when heavier loads such as those of infusion pumps or cylindrical tanks are placed upon a stand.

The present invention addresses these problems by providing an I.V. stand which is easily capable of accommodating infusion pumps and other modern I.V. equipment. Another aspect of this invention is to provide an I.V. stand which rolls smoothly, easily and stably over irregular surfaces such as carpet and which is capable also of being stably transported up and down stairs by the patient or others. A removable support platform is provided which easily accommodates the mounting of cylindrical tanks, thereby permitting ready conversion of the stand for multiple applications. This invention provides a device which accomplishes substantial improvements in mobile stand technology using simple materials and manufacturing techniques.

SUMMARY OF THE INVENTION

A cart for the transport of intravenous equipment such as infusion pumps, bags, bottles, as well as cylindrical gas storage tanks, is provided with an upstanding pole extending from the junction of a T-shaped base. A horizontal base member which forms part of the T-shaped base has large diameter non-swivelable wheels located at either end thereof while the leg which forms part of the T-shaped base has a castering wheel located at the end. By providing a pole which extends from the junction of the T-shaped base, the infusion pump and other associated equipment may be located at approximately the center of support of the triangular planform defined by the location of the three wheels. The pole extends vertically upward from the junction of the base and is slidably adjustable to vary the height primarily of the I.V. solution. A handle is provided on the pole for ease of maneuvering the stand. A skid extends from the junction of the base opposite the base leg horizontally and angles upwardly and inwardly towards the pole. This skid serves to ease the transport of the stand up and down stairs in conjunction with the large wheels and handle. A removable support platform for the transport of gas cylinders is also provided.

These and other features and advantages of the invention will appear more fully from the following description made in conjunction with the accompanying drawings wherein like reference characters refer to the same or similar parts throughout the several views.

BRIEF DESCRIPTION OF THE DRAWINGS

FIG. 2 is a sectional view taken along line 2-2 of FIG. 1.

FIG. 7 is an elevation of the longitudinal base member as shown in FIG. 1.

FIG. 8 is a bottom plan view of the longitudinal base member as shown in FIG. 1.

DETAILED DESCRIPTION OF THE PREFERRED EMBODIMENT

Figure 1:
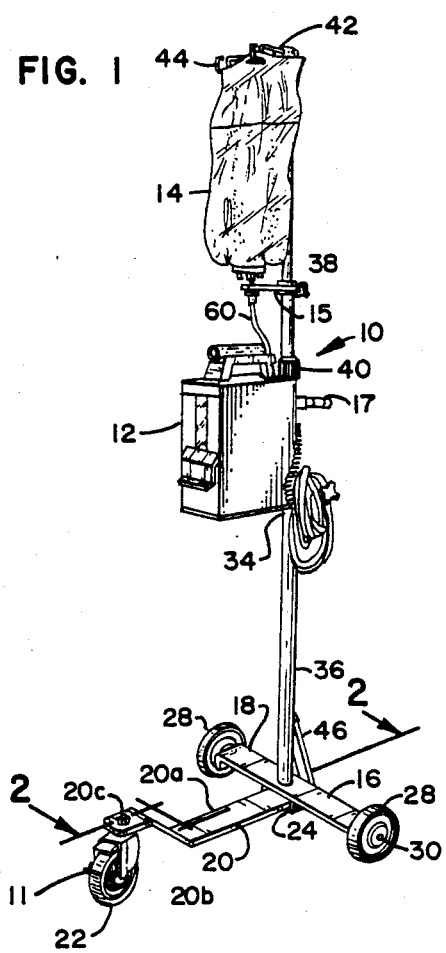
FIG. 1 is a perspective view showing the stand of the present invention.
Figure 3:
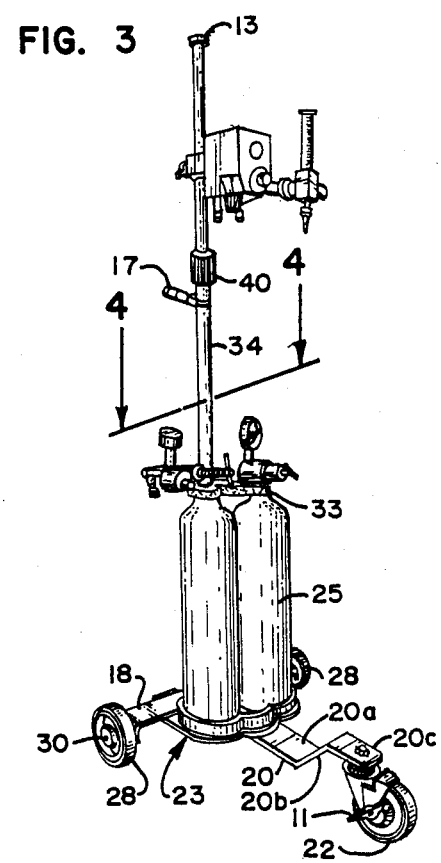
FIG. 3 is a perspective view of an alternate embodiment of the stand of FIG. 1 as used to transport cylindrical tanks.

The instant invention, generally designated 10, is designed to carry an infusion pump 12 and one or more I.V. bags 14. Such pumps 12 and bags 14 are well known and hence, will not be described in more detail. The base 16 of stand 10 is generally T-shaped and is comprised of a longitudinal base member 18 joined at a junction to a base leg 20. Base leg 20 is comprised of a main portion 20a extending horizontally from the junction with base member 18, an inclined portion 20b and a wheel mounting portion 20c which is also horizontal and serves as a mount for rotatable and revolvable caster wheel 22. A brake assembly 11 is attached to caster wheel 22 to permit immobilization of the entire stand 10.

Figure 6:
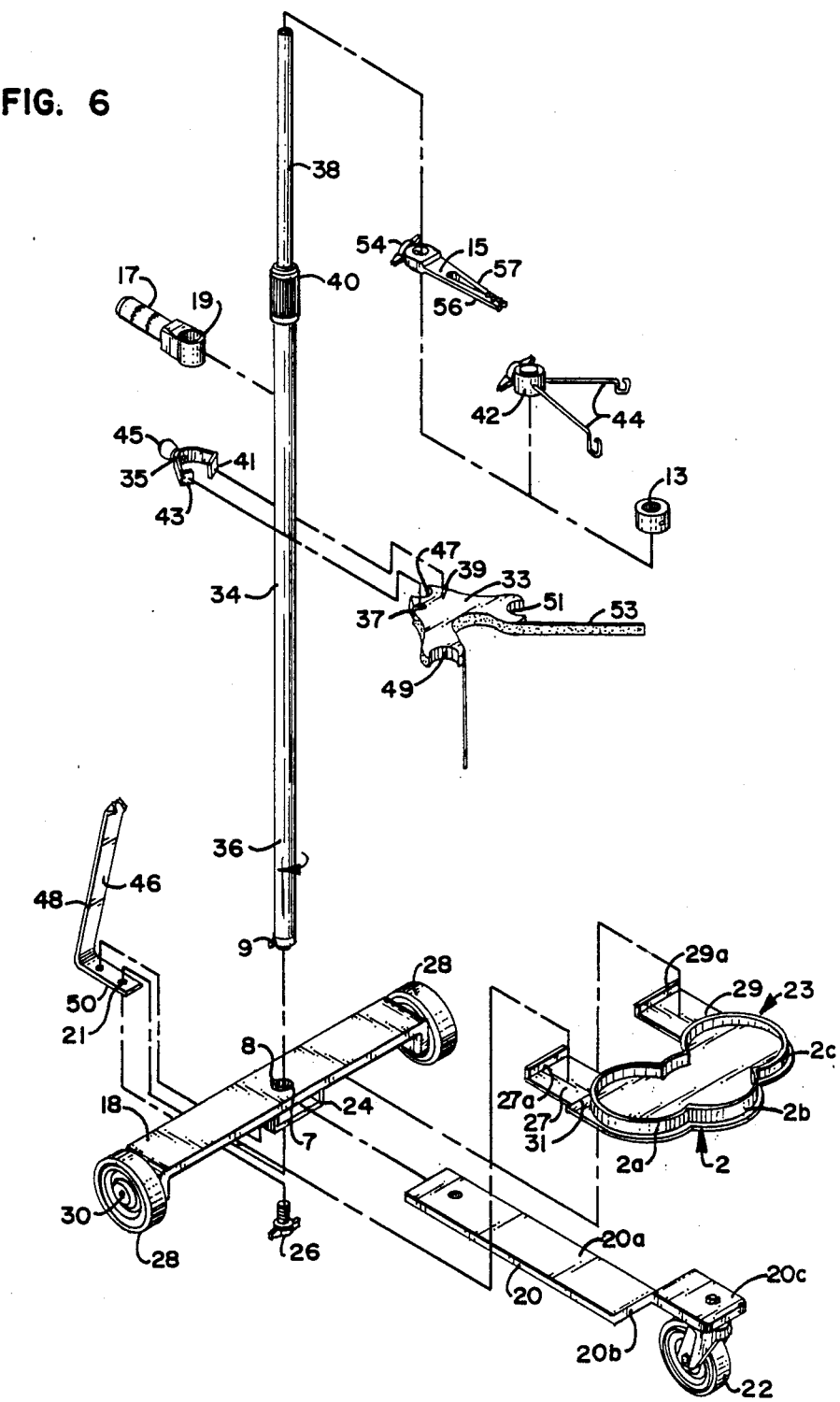
FIG. 6 is a perspective view shown in expanded form of the stand as depicted in FIG. 3.
Figure 9:
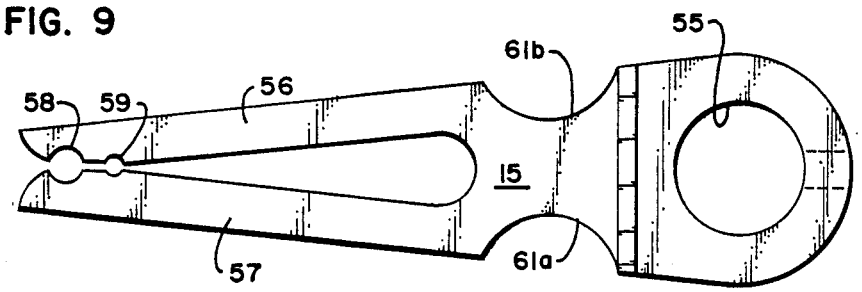
FIG. 9 is a plan view of the support clip as depicted in FIG. 6.
Figure 10:
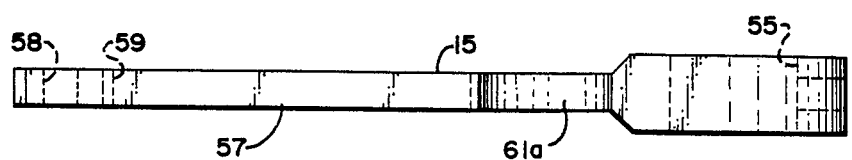
FIG. 10 is an elevation of the support clip as depicted in FIG. 9.

As best seen in FIGS. 6, 7 and 8, a mounting plate 24 is located at the junction of base member 18 and base leg 20 and serves to permit the alignment and attachment of both pole 34 as well as base member 18 to base leg 20. Mounting plate 24 is centrally located on the bottom of base member 18, and is formed in a generally "U" shape, thereby creating a left side 3, a bottom surface 4, and a right side 5. A small orifice 6 is machined near the center of bottom surface 4, the orifice 6 being coaxially aligned with a large orifice 7 passing through the center of base member 18. In order to prevent the undesired rotation of pole 34, a slot 8 radially adjoins the circumference of large orifice 7, the slot 8 accommodating a protrusion 9 located near the base of pole 34. Once pole 34 is placed through large orifice 7, a threaded fastener 26 is inserted through small orifice 6 and rotatably inserted into the compatibly threaded interior of pole 34. Rigid attachment is accomplished by means of fastener 26, which may be tightened or loosened by hand, thereby permitting simple assembly and disassembly which will allow the invention 10 to be transported in a compact, portable configuration.

Wheels 28 are located at either end of base member 18 and revolve about axle 30 which is in turn affixed to base member 18 by passing through orifice 1. It is to be noted that axles 30 are fixed and thus, wheels 28 are limited to rotation in a fixed plane relative to one another and to stand 10.

As mentioned previously, pole 34 is mounted to base member 18 and secured through mounting plate 24. Pole 34 is comprised of a bottom section 36 and a top section 38 which are slidably connected by telescopic joint 40 of conventional construction. Joint 40 allows the bottom and top sections 36 and 38 to be slidably adjusted relative to one another in order to vary the height of bag 14. A fitting 42 is located at the top of section 38 from which extend hooks 44, the hooks 44 serving to support one or more I.V. bags 14. A cap 13 may also be placed on top of section 38 when fitting 42 is not in use.

A support 15 may also be placed over section 38 as needed. As best seen in FIGS. 1, 6, 9 and 10, the support clip 15 contains mounting hole 55 and slides over section 38 and is secured by thumb screw 54. The support clip 15 is formed as a first arm 56 and an opposing second arm 57, the arms being composed of a resilient material tending to resist separation of the arms. The two arms taper to form two sets of opposed planforms, thereby creating a large grip 58 and small grip 59. In operation, grip 58 secures the spike of the I.V. set or the small grip 59 may be used to secure the I.V. line 60. A one-half radius 61a and 61b located on each side of clip 15 allows the index and middle finger of a human hand to grip the support 15 while the thumb snaps the spike site into grip 58.

Another aspect of the present invention is handle 17, which may be attached anywhere along pole 34 and adjusted at will, by sliding, along the length of pole 34, the attachment being accomplished by means of pole gripping element 19. Gripping element 19 is a hollow cylinder compatibly sized to encompass pole 34, and is mechanically interconnected to handle 17 such that rotation of handle 17 will permit increasing or decreasing the rigidity of the interconnection between pole 34 and gripping element 19.

A skid 46 is utilized to ease the transport of stand 10 over stairways and is comprised generally of an attachment flange 50 which extends horizontally from the junction of base member 18 and base leg 20, and then angles acutely upwardly thereby forming angled portion 48 towards pole 34, as can be seen particularly in FIG. 2. As shown in FIG. 6, skid 46 is mounted by inserting attachment flange 50 between bottom surface 4 and base member 18. A mounting hole 21 on attachment flange 50 is coaxially aligned with large orifice 7 and small orifice 6, thereby permitting fastener 26 to rigidly secure skid 46 to base member 18.

Figure 4:
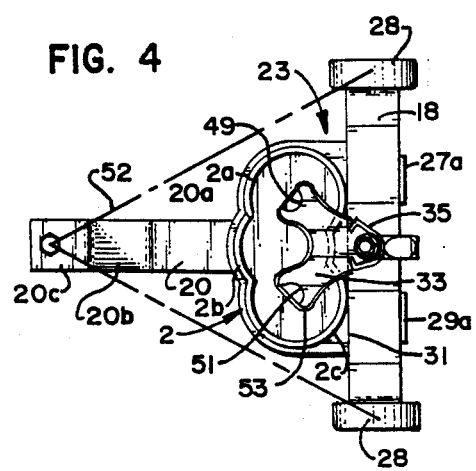
FIG. 4 is a sectional view taken along line 4-4 of FIG. 3.
Figure 5:
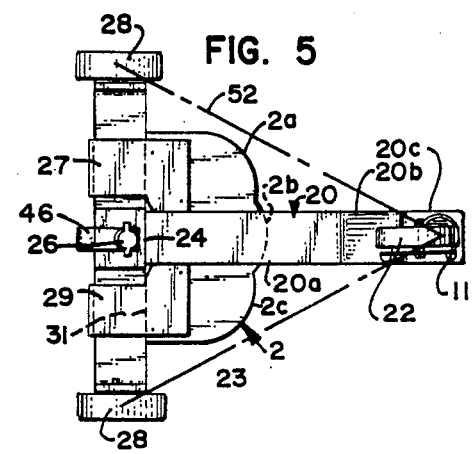
FIG. 5 is a bottom plan view of the stand as depicted in FIG. 3.

FIGS. 4 and 5 show in particular the outline of the area of support 52. Any substantial weight located outside of that outline will, of course, result in instability of stand 10. By locating pole 34 at the junction of base member 18 and base leg 20, the location of infusion pump 12 is at approximately the center point of the area of support indicated by numeral 52. This results in the maximum stability of stand 10. As seen in FIG. 2, a horizontal force acting against pole 36 will act substantially through the axis 62 of wheel 22. Pole 36 is anchored at the centerline of wheels 28, thus producing no pitching movement upon the application of a horizontal force. The triangular planform therefore allows, in conjunction with this particular wheel and base arrangement, for ease of maneuvering the stand over irregular surfaces, stairs and the like.

Another novel feature of the present invention resides in the gas cylinder support mechanism shown generally at 23. The support mechanism includes a support tray 2, the tray being formed generally as three overlapping circular planforms shown in FIG. 6 as first receptacle 2a, second receptacle 2b and third receptacle 2c. In order to preserve the balance of stand 10, a single cylinder should be placed in second receptacle 2b, whereas two cylinders should be placed individually in first receptacle 2a and third receptacle 2c, respectively. The cylinders 25 are of standard shape and dimension and fit snugly into the circular receptacles.

The support tray 2 is rigidly attached to a left bracket 27 and a right bracket 29, the two brackets being substantially planar, mirror images of each other. As best seen in FIG. 5, the brackets are mounted on the bottom surface of support tray 2, and are separated substantially symmetrically so as to encompass a distance slightly greater than the width of base leg 20, thereby preventing lateral movement of the tray 2.

Each bracket 27 and 29 includes a lip, 27a and 29a, respectively, which forms a substantially perpendicular protrusion from the parent bracket. The lips 27a and 29a are located on the brackets such that the distance between the lip and the rear edge 31 of tray 2 is only slightly greater than the width of base member 18, thereby preventing longitudinal movement of the tray 2. The tray 2 is constructed of a dense material, thereby trending to resist vertical movement of the mounted tray, such tendency being enhanced by the weight of the cylinder(s) 25 which may be mounted in the receptacles. Thus, the tray 2 is constrained in all three axes without the use of any fasteners whatsoever.

The mounted cylinder(s) 25 are stabilized by neck brace 33, which is affixed to pole 34 by clamp 35. Neck brace 33 includes a left slot 37 and a right slot 39, the slots corresponding to left tab 41 and right tab 43 of clamp 35. Each tab fits into the corresponding slot. The rotation of clamp handle 45 urges concavity 47 of neck brace 33 toward pole 34, thereby forming a relatively rigid interconnection.

The cylinder(s) 25 are secured to neck brace 33 by placing the stem of the cylinder within either first semicircular fillet 49 or second semicircular fillet 51. A hookable tape fastener 53 is used to secure the cylinder stem within each fillet and to permit its easy removal.

While the preferred embodiments of the present invention have been described, it should be understood that various changes, adaptions and modifications may be made therein without departing from the spirit of the invention and the scope of the appended claims.

I claim:

1. A portable stand for support of an intravenous infusion pump and associated equipment, the stand comprising:
   (a) a longitudinal base member having first and second ends;
   (b) a base leg extending perpendicularly from and releasably interconnected to the base member, the base leg having a first end releasably interconnected to the base member, the base leg including a main portion proximate the first end and a wheel mounting portion proximate an opposite second end, mounting plate means interconnected the base leg to the base member, the mounting plate means including a mounting plate fixedly attached to the longitudinal base member and cooperating with the base member to form a cavity for slidably receiving the first end of the base leg thereby confining the base leg between the mounting plate and the base member, the mounting plate having a first orifice defined therein, the base leg having a second orifice defined therein located proximate the first end of the base leg, and the base member having a third orifice defined therein, the first, second, and third orifices being coaxially aligned;
   (c) first and second wheels rotatably attached to the first and second ends, respectively, of the longitudinal base member, each of the first and second wheels being confined to rotation in a fixed plane relative to one another and the stand;
   (d) a pivotal caster wheel attached to the wheel mounting portion proximate the remote end of the base leg; and
   (e) a pole having a lower end and an upper end, the lower end of the pole being slidably received in the second and third orifices, the pole extending vertically upward from the base member, the lower end of the pole including a first end portion and a second end portion of larger diameter than the first end portion, shoulder means being formed intermediate of the first and second end portions and cooperating with the stand for vertically supporting the pole, the lower end of the pole being releasably interconnected to the remainder of the stand at a location lower than the wheel mounting portion of the base leg, whereby the pole is stable with respect to the remainder of the stand, even during assembly or disassembly of the stand.

2. The stand of claim 1, the mounting plate being formed substantially as a U-shaped bracket, the mounting plate being rigidly attached to the base member, and adapted to receive the base leg, thereby confining the base leg between the mounting plate and the base member.

3. The stand of claim 2, including a threaded fastener and a threaded receptacle within the pole interconnecting the mounting plate, the base leg, and the base member to the pole, the threaded fastener being insertable into the threaded receptacle within the pole.

4. The portable stand of claim 3, wherein the orifice within the base member contains a keyway, the keyway extending radially from and joining the orifice, the keyway being adapted to receive a protrusion on the pole, thereby preventing rotation of the pole when the pole is mounted on the base member.

5. The portable stand of claim 4, further comprising a handle, the handle extending substantially perpendicularly from a longitudinal axis defined by the pole.

6. The stand of claim 5, wherein the handle includes a gripping element, the gripping element being interconnected with a rotatable portion of the handle such that the gripping element may be urged to tightly encompass the pole when the handle is rotated.

7. The portable stand of claim 6, wherein the first wheel, the second wheel and the caster wheel form a substantially triangular platform, the base member forming a first side of the triangle such that a center of mass as defined by the equipment supported by the pole resides within the triangular platform.

8. The portable stand of claim 7, further comprising a skid, the skid being formed as a substantially continuous strip, the strip having been deformed at an acute angle, a first end of the strip being secured by the fastener passing through the mounting plate and a second end of the strip being pressed against a portion of the pole, the skid thereby being positioned at the first end of the base leg and opposite the caster wheel, thereby permitting the stand to slide along the skid without interaction with the caster wheel.

9. The stand of claim 1, further comprising a cylinder support mechanism, the cylinder support mechanism being formed substantially as a tray, the tray including three overlapping circular planforms, each planfrom being adapted to receive a cylindrical container.

10. The portable stand of claim 9, wherein the tray includes a left bracket and a right bracket, each bracket being a substantially planar sheet, the brackets being mounted symmetrically on the tray such that the tray may be placed on the base leg, the brackets cooperating with the base member for preventing lateral movement of the tray.

11. The stand of claim 10, wherein each bracket includes a lip, the lip being substantially perpendicular to the planar sheet, the lip being displaced from the support tray such that the lip and the support tray encompass the base member such that when the tray is mounted on the base leg that the lip and the support tray constrain the tray from movement about the base member.

12. The stand of claim 1, further comprising a neck brace, the neck brace being comprised of a substantially planar member, the planar member being adapted to grip the pole, the planar member having a series of concavities adapted to receive cylindrical shaped objects and stabilize said objects in relationship to the pole.

13. The stand of claim 12, including a strip of flexible, hookable cloth fastener means for bridging the concavities whereby objects can be restrained within the concavities of the neck brace.

14. The stand of claim 8, further comprising a support clip, the support clip being slidably mounted on the pole, the support clip being formed as a first and second resilient, tapering, opposed arms, the arms containing opposed semicylindrical concavities suitable for retaining tubing in a fixed position in relationship to the equipment being supported by the stand.

15. The stand of claim 14, wherein the support clip further comprises a first half radius and a second half radius, the first radius being formed into the first opposed arm, the second half radius being formed into the second opposed arm, the first and second radius permitting grasping by a human hand so as to facilitate insertion of the retained tubing.

16. The stand of claim 1, wherein the main portion of the base leg has a greater longitudinal extent than the wheel mounting portion of the base leg.

17. The stand of claim 1, wherein the lower end of the pole is threaded, a threaded fastener cooperating with the threaded lower end of the pole to threadedly fasten the lower end of the pole to the stand at a location below that of the wheel mounting portion of the base leg.

18. The stand in accordance with claim 1, wherein the base leg is substantially rectangular in cross-section, the mounting plate and the base member engaging oppositely facing major surfaces of the base leg.

19. The stand in accordance with claim 1, wherein the pole includes telescoping members so as to be adjustable in height.

20. The stand of claim 1, the second orifice being of lesser diameter than the second end portion of the lower end of the pole and of larger diameter than the first end portion of the lower end of the pole, the third orifice being of larger diameter than the second portion, whereby upon insertion of the pole into the second and third orifices the shoulder means rests on the base leg.

* * * * *